United States Patent
Meyer

(10) Patent No.: US 6,345,982 B1
(45) Date of Patent: Feb. 12, 2002

(54) DENTAL LIGHT CONTROLLER AND CONCENTRATOR

(75) Inventor: Alvin Meyer, deceased, late of San Mateo, CA (US), by Bernice S. Meyer, legal representative

(73) Assignee: Darcy M. Dunaway, San Mateo, CA (US)

( * ) Notice: Subject to any disclaimer, the term of this patent is extended or adjusted under 35 U.S.C. 154(b) by 0 days.

(21) Appl. No.: 09/388,396

(22) Filed: Sep. 1, 1999

(51) Int. Cl.[7] .............................. A61C 1/00; A61C 3/00
(52) U.S. Cl. ......................................... 433/31; 433/141
(58) Field of Search ............................ 433/29, 30, 31, 433/141, 229; 359/885, 892, 851, 867

(56) References Cited

U.S. PATENT DOCUMENTS

| | | | | |
|---|---|---|---|---|
| 3,708,222 A | * | 1/1973 | Stern | 359/851 |
| 4,093,346 A | * | 6/1978 | Mishino et al. | 359/851 |
| 4,445,858 A | | 5/1984 | Johnson | 433/141 |
| 4,522,594 A | * | 6/1985 | Stark et al. | 433/141 |
| 4,592,726 A | * | 6/1986 | Brilliant | 433/31 |
| 4,615,679 A | | 10/1986 | Wyatt | 433/229 |
| 4,640,685 A | | 2/1987 | Croll | 433/141 |
| 4,662,842 A | | 5/1987 | Croll | 433/141 |
| 4,673,353 A | | 6/1987 | Nevin | 433/90 |
| 4,900,253 A | | 2/1990 | Landis | 433/30 |
| 4,989,125 A | * | 1/1991 | Cobb, Jr. et al. | 359/851 |
| 5,288,231 A | | 2/1994 | Kuehn | 433/29 |
| 5,509,800 A | | 4/1996 | Cunningham et al. | 433/29 |
| 5,730,599 A | | 3/1998 | Pak | 433/215 |
| 5,749,724 A | * | 5/1998 | Cheng | 433/29 |
| 5,791,898 A | | 8/1998 | Maissami | 433/164 |
| 5,803,729 A | | 9/1998 | Tsimerman | 433/29 |

* cited by examiner

*Primary Examiner*—Todd E. Manahan
(74) *Attorney, Agent, or Firm*—Flehr Hohbach Test Albritton & Herbert LLP

(57) ABSTRACT

A light shield device (13) which is attached to light wands (30) of various diameters to filter and redirect reflected light. The shield has a planar part (13) with an attached retainer column (20) mounted in an off-center location, a see-through mirror (16) in a central location, and a reflective Fresnel lens configuration (14) at its outer perimeter. The device is formed of plastics which filter some radiation. The shield permits an operator to monitor light applications without harmful eye irritations.

19 Claims, 3 Drawing Sheets

DENTAL LIGHT CONTROLLER AND CONCENTRATOR

BACKGROUND—Field of Invention

This invention pertains to dental instruments, more specifically, to a means for protecting the operator's eyes from high intensity lights which are commonly used in dentistry.

BACKGROUND—Description of Prior Art

Dentists are restoring many tooth cavities with restorative compositions which polymerize and harden when exposed to selected bright lights. Appropriate bright light is available from the distal end of a portable light wand. However, reflections of such bright light from a mouth often reach the dentist's eyes where they are intense enough to be irritating. The portion of the light which is most effective as a stimulus for the viscous restorative is the blue wave lengths which are traumatic for the operator's eyes. Never-the-less, it is imperative that the operator view the treatment area clearly with adequate light. Also, if a polymerizing light is held too far from the restorative the intensity and effectiveness of its beam will decrease. Further, the light wand should not be close enough to contact the restorative since contact from a wand assembly will damage the surface form of the restoration. Thus, protective shields have been proposed to protect the operator's eyes from such harmful reflected radiation.

Available shields exhibit detrimental features. Many shields are designed as cones or parabolic forms which are cumbersome because they require more space and weight. Thus they tend to contact the restorative composition which is likely to cause damage. Prior shields also reflect randomly and generate secondary reflections from glossy mouth tissues. This shield provides a see-through segment with reduced intensities and filtration of blue light for safe viewing of the treatment field but others do not enable adequate monitoring of the treatment field.

U.S. Pat. No. 4,445,858 to Johnson (1984) describes a frustro-conical shield affixed to a fiber optic light wand with a reflective underside. Its conical reflective surface will direct light in arbitrary, unfocused patterns and it is made of opaque polymers which do not provide an adequate view treatment field.

U.S. Pat. No. 4,615,679 to Wyatt (1986) details a frustro-parabolic attachment for a light wand which does not reflect or focus extraneous light. It is formed of a copolymer of ethylene and vinyl acetate which will not provide an adequate view of the treatment field.

U.S. Pat. No. 4,640,685 to Croll (1987) discloses a paddle to be held between a field of treatment and an operator's eyes. No provision is made to reflect or concentrate stray light. Usually, an operator holds and directs a light wand in one hand and uses the other to deflect lips, tongue and cheeks to permit accessibility. However, it is cumbersome and difficult to control the wand and tissues and also hold the paddle.

U.S. Pat. No. 4,662,842 to Croll (1987) shows a device which purports to obviate the need for a third hand by attaching a paddle to a finger ring. It is made of orange plastic as a light filter, but is awkward and does not adequately collect or redirect reflected light.

U.S. Pat. No. 4,673,353 to Nevin (1987) offers a syringe with an opaque outer veneer to protect the operator's eyes and a light bearing plunger to activate the hardening of the composition injected by the syringe. The orifice of the cavity tends to be obscured by the opaque cylinder and to make a disruptive contact with a formed restorative composition.

U.S. Pat. No. 4,900,253 to Landis (1990) discloses pigments affixed to a dental mirror which are intended to modify damaging light rays. Because of its limited dimensions, such a mirror will modify some, but neither all nor most of the light reflected.

U.S. Pat. No. 5,288,231 to Kuehn (1994) shows a flat shield of crystalline styrene plastic with crossing slits through which a light wand may be inserted. It offers no light collecting or redirecting advantages.

U.S. Pat. No. 5,509,800 to Cunningham (1996) shows a flat, pigmented and transparent planar device with no collecting or reflecting characteristics.

Additionally, operators have used eyeglass covers and pigmented eyeglass lenses to protect their eyes, but such covers and lenses will not adequately reflect the reflected light.

OBJECTS AND ADVANTAGES

Accordingly, several objects and advantages of my invention are:

1. to provide a way to protect an operator's eyes from bright lights used in dental procedures,
2. to provide a means to collect, redirect and utilize reflected light which would otherwise be wasted and
3. to provide a device to focus the primary beam to a limited area.

Still further objects and advantages will become apparent from a consideration of the ensuing description and drawings.

REFERENCE NUMERALS

Figure 1:
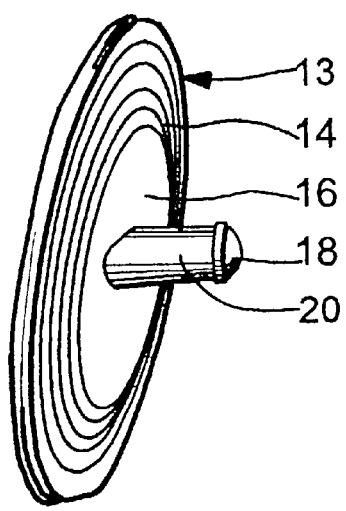
FIG. 1 shows an isometric view of shield assembly for a light wand according to the invention.
Figure 4:
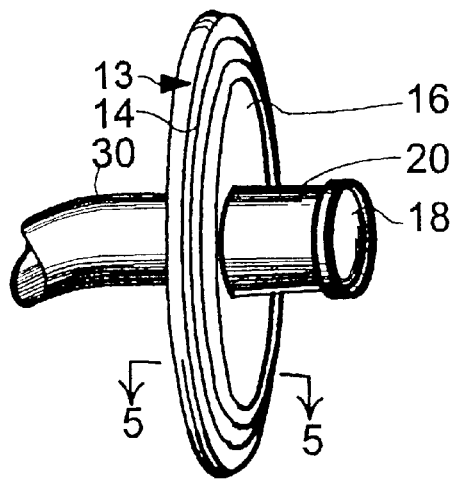
FIG. 4 is an isometric view of the shield assembly of FIG. 1 attached to a light wand.

13 Planar shield
14 Fresnel surface zone of shield

15 Reflective coat
16 Clear, see through, zone of shield
17 Groove for lens
18 Focusing lens
19 Collar to support lens
20 Conical retainer column
21 Lumen of collar
22 Cylindrical padding collet for small diameter light wand
24 Lumen of collet
26 Annular retainer for collet
28 Helical ribbon of columnar retainer
29 Helical slit to divide columnar retainer wall
30 Light wand
32 Retainer wall divided into parallel bars for elasticity
34 Parallel slits to provide for expansion and elasticity of retainer wall
36 Bead to contact light or padding collet
38 Restorative composition in tooth cavity
40 Segment of a dental arch

SUMMARY

In accordance with the invention, I provide a shield to protect an operator's eyes from reflected light while an operator is using a powerful light wand to initiate polymerization of photo-responsive resins within a tooth cavity. Secondarily, the shield collects, focuses, and redirects wasted light reflections to reinforce a primary beam. The shield is a flat, planar surface somewhat ovoid in its outline. Its central reflective surface is lightly coated with a reflective substance to form a see-through mirror developed between two other zones of its planar surface: the outer zone of the planar surface is concentrically indented in the manner of a Fresnel lens to focus reflected light toward a treatment area and it is heavily coated with reflective substances; and a truncated conical retainer at its inner zone. The retainer is divided to allow its elastic walls to be distended in order to form an active clamp on the tubular light wand. Two other unique features are shown in an eccentric attachment position of the base of the conical retainer to the smooth see-through zone of the shield and in its non-perpendicular angle of departure from the plane of the shield, approximately 15°. The angular departure allows an operator to rotate the device on the light wand to accommodate a left or right cheek presence. The non-perpendicular angle of departure places the shield parallel to the viewer's eyes while the light beam is angularly directed toward the treatment zone.

Optionally, a focusing lens is attachable by an elastic collar at the distal end of the conical retainer which can concentrate a beam, reduce waste light and improve its potency as a photo-stimulus. Embodiments are shown to provide versatility of attachment of conical retainers to a variety of light wands.

PREFERRED EMBODIMENT—DESCRIPTION

Figure 2:
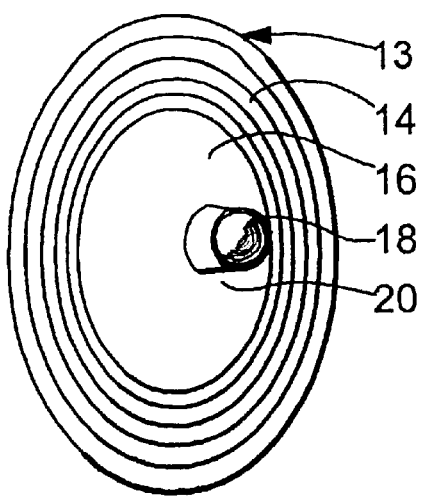
FIG. 2 shows a plan view of FIG. 1 showing the outline of the shield and the eccentric posture of the retainer column.

The preferred embodiment, as shown in FIGS. 1 and 2, consists of two components molded as a unit and two free-standing parts. A shield 13 and its retainer 20 are molded of crystalline styrene, orange acrylic, or other transparent materials known to attenuate blue light. It has a flat shape with two major opposing, generally planar, surfaces. It has a somewhat ovoid outline and, when viewed in a direction perpendicular to its surface, its size is approximately four by six centimeters with a thickness of the from 2 to 5 mm. It is smooth on its central area surface where, with reflective veneer 15, it forms a see-through mirror. On its outer surface, a zone is molded with elevations, surface configurations, and indentations 14 and is thickly coated with a bright metallic veneer to form a reflective surface in the manner of a Fresnel lens with a focal point slightly beyond the distal end of the dentist's light wand 30. At a position off center is molded a truncated cone 20 about 1.3 cm diameter at its attached base and about 7 mm diameter at its distal end. The base of retainer cone 20 attaches to planar shield 13 off center such that more of the shield plane is on the first surface segment than is on its second surface segment. Since molded styrenes in thin segments are elastic, the cone has helical slot 29 to form opposing and helical elastic clamping retainer ribbon 28 for the shield assembly when the ribbons are distended and positioned on light wand 30. The helically positioned diameters are reduced as it proceeds distally so as to generate a truncated conical form which allows it to be distended when forced on light wand 30 and then, elastically, to clamp light wands of various diameters. The surface finish of slotted cone 20 is dull to preclude reflections of blue light in lateral directions.

A sponge rubber collar 19 is provided to be manually stretched over the distal end of the columnar retainer 20 to provide additional frictional pressure of retainer wall 32 against the light wand 30. Its lumen 21 presents a groove 17 into which an exchangeable lens 18 may be inserted to focus the primary beam to a smaller and more intense light.

Between Fresnel zone 14 and retainer 20, planar surface 13 has a mirror-smooth zone 16 which reflects some of the light but transmits enough light to enable the operator to view the treatment field.

Figure 7:
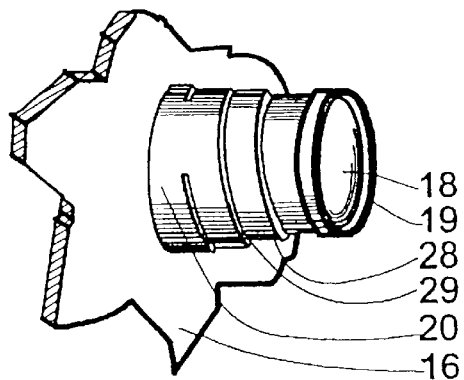
FIG. 7 shows segment of the shield and a helical slit in the retainer column.
Figure 8:
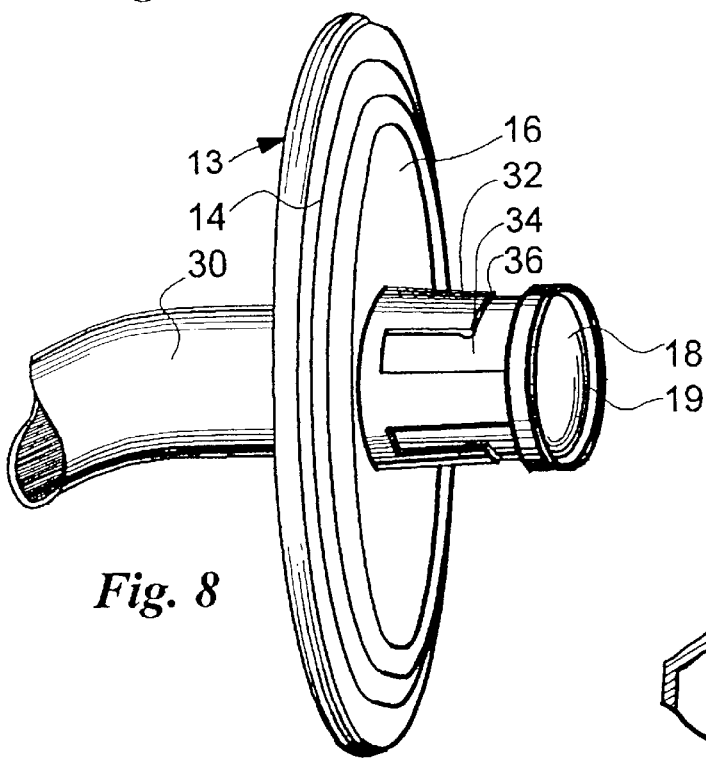
FIG. 8 shows an isometric view of an alternative embodiment according to the invention where the retainer column is divided into several elastic strips.
Figure 10:
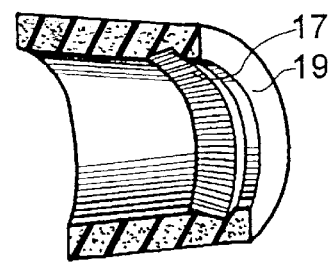
FIG. 10 shows a sectioned view of the collar of FIG. 9 and its lens holding groove.

As shown in FIG. 7, conical retainer 20 is divided into a helical ribbon 28 by a helical slit 29 to utilize the elasticity of molded styrene to develop a coiled clamping of wand 30. The diameters of the helical coils are reduced as the helix extends from the attached base of the retainer. Alternatively, retainer 20 is divided by parallel slits 34 into opposing and converging bars 32 as shown in FIG. 8 to provide a clamping constriction when distended to stretch over wand 30. The distention and clamping force of bars 32 is augmented by semi-circular beads 36 at the free ends of each of the bars.

The distal end of retainer 20 is fitted with circular collar 19 of elastic material such as rubber or foamed plastic as shown in FIGS. 7–10. Inner surface 21 of collar 19 adapts to retainer 20 relying upon its elasticity for frictional retention and has trenched groove 17 near its distal edge to clamp lens 18.

Figure 9:
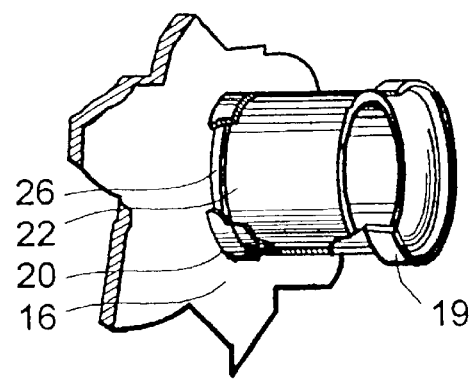
FIG. 9 is cut-away view of a columnar retainer to show the collet of FIG. 3 and a retaining annular ring and an elastic lens holding collar at its distal end.
Figure 11:
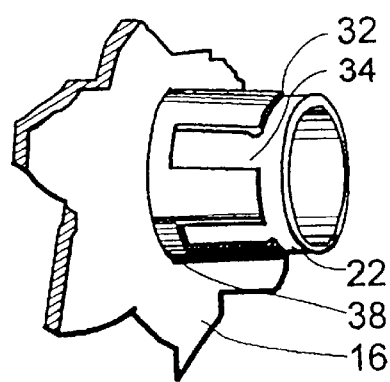
FIG. 11 shows a segment of the shield as of FIG. 8 and a detail of retainer.
Figure 12:
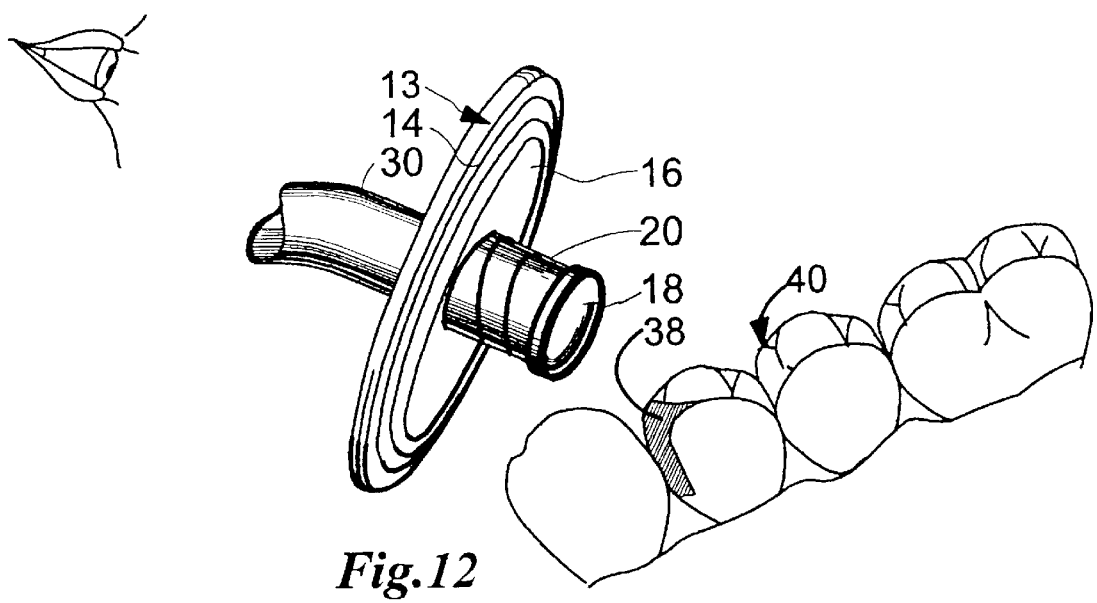
FIG. 12 shows the shield of FIG. I interposed between the operator's eyes and the light reflected from the treated mouth tissues.

As shown in FIGS. 9 and 11, a tubular collet 22 of elastic material such as rubber or foamed plastic is provided as padding for light wands with small outer diameters. An elastic band 26 is provided as an annular positional retainer for the collet. Conical retainer 20 will then fit snugly over the padded wand.

PREFERRED EMBODIMENT—APPLICATION

Given a tooth cavity appropriately cleansed and shaped, an operator will prepare light wand 30 for usage. If the outer diameter of the shaft of the light wand is small, collet 22 is stretched around the shaft as padding. Elastic band 26 is stretched around the shaft to prevent displacement of the collet. Shield 13 is applied by inserting the distal end of light wand 30 into and through the lumen of retainer 20 while stretching helical segment 28 or retentive arms 32 to develop a frictional clamp around the shaft. Light travels through the fiber optic system of the wand and emanates as a beam to be projected upon the tooth and positioned restoratives.

Shield assembly 13 is rotated around wand 30 to relocate its wider dimension away from a patient's face and position the wand very close to restorative composition 38. The operator directs the beam from the distal end of wand 30 toward the composition 38 as shown in FIG. 13. The field of light application is safely envisioned through smooth central zone 16 of the shield. Safety derives from the capability of the shield's resin to filter most blue light and from a thin veneer of reflective metal over see-through zone 16 which reflects much of the light back toward the treatment field. Simultaneously, outer zone 14, a reflective Fresnel lens, will redirect stray light back toward the treatment field to augment the intensity of the primary beam.

Optionally, collar 19 may be stretched across the distal end of retainer 20 to supplement the clamping forces. For smaller beams, lens 18 may be inserted into trench 17 to be retained within collar 19. The beam focus is adjusted by sliding collar 19 and the entrenched lens along the shaft to or from the light source to generate a concentrated light pattern with increased intensity and a smaller illuminated field. The smaller field will reduce light reflections from adjacent tissues.

Shield 13 and its eccentrically attached retainer column 20 are rotated around the shaft of light wand 30 to achieve the best adaptation for the patient's comfort, the shortest possible projection distance and the operator's safety. The diameter of the beam may be altered by sliding retainer 20 to or from the light source at the distal end of shaft 30 to increase of decrease the lens-to-source dimension.

Figure 5:
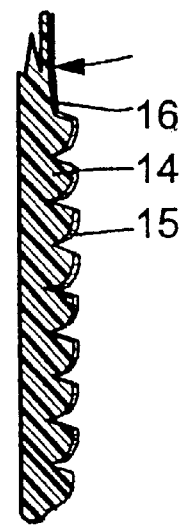
FIG. 5 is a sectional view of the shield of FIG. 4.
Figure 3:
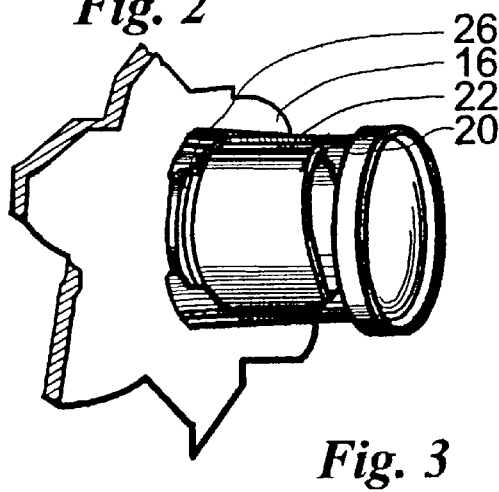
FIG. 3 shows a segment of the shield with an attached retainer column and a cut-away view of the retainer.
Figure 6:
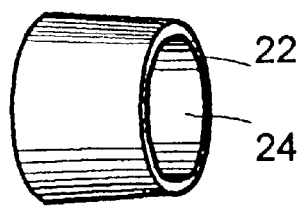
FIG. 6 shows an elastic collet to be inserted when a light wand is smaller than the lumen of the retainer column shown in position in FIG. 3.

Increments of photoreactive restorative compositions 38 are placed within the tooth cavity and illuminated to excite polymerization and hardening of the resin. The operator safely views the field of treatment through central zone 16 of planar shield 13 which has been lightly coated with reflective metal 15 to create a see-through mirror as shown in FIG. 5. The volume of reflected light is reduced because much of that light is redirected toward the treatment field. The operator's eyes are protected from blue light irritation by the filtering capabilities of the resin chosen for the shield and by the reduced volume of light reflected back toward the operator.

All parts are removed and sterilized before being reused.

CONCLUSIONS, RAMIFICATIONS AND SCOPE

Accordingly, it can be seen that I have provided protection for an operator's eyes while strong light is directed toward composite resin restoratives, a means to collect and return reflected light toward the target area, and an appended lens to control the diameter and intensity of a primary. While attenuating blue light, which might harm the operator or bystanders, and while reducing the volume of irritating light, the improved light shield provides a window through which the operational field may be monitored.

My shield provides for a controlled redirection of waste light to support radiation from the principal without reflecting it randomly or generating secondary reflections from glossy mouth tissues This shield provides a see-through segment with reduced intensities and filtration of blue light for safe viewing of the treatment field while still allowing for the necessary monitoring of the treatment field. Since this shield mounts on the stem of many sizes of wands, both wand and shield are supported with one hand. Thus, the operator's other hand is free to deflect the patient's cheek or tongue.

Although the description above contains many specificities, these should not be construed as limiting the scope of the invention but as merely providing illustrations of some of the presently preferred embodiments of this invention. Various other ramifications are possible within its scope. For example:

- the base plastic can be impregnated with dyes capable of absorbing blue light,
- the shield may be formed of flexible plastic;
- the shield may be formed of any transparent material such as pigmented glass;
- the Fresnel ridges may be on either face of the planar shield;
- the reflective coat of metal may be applied on the proximal side of the planar shield;
- the outline of the planar shield may be varied from ovoid to free form to secure intimate adaptation to the patient's cheek planes or; for simplicity during manufacturing, it may be a rectangle, parallelogram or the like or;
- the shield may be used in non-dental applications such as photographic illumination to generate high-lights.

Thus, the scope of the invention should be determined by the appended claims and their legal equivalents rather than by the examples given.

I claim:

1. A device for protecting the eyes of operators and bystanders from such harm as may result from viewing bright light emanating from a light wand to a work area and reflected back from that work area, comprising:

a semi-transparent light shield said shield having two opposing major surfaces and is formed with an aperture for said light wand to pass therethrough, said shield having a clear area surrounding said aperture and, a reflective area surrounding said clear area, said reflective area comprising Fresnel ridges.

2. The device of claim 1 wherein said shield is molded of plastics.

3. The device of claim 1 further includes a reflective coating on said clear area for reflecting a portion of the light reflected from said work area and allow the remaining fraction of light to pass through said clear area.

4. The device of claim 1 wherein said shield attenuates blue light.

5. The device of claim 1, wherein said shield further comprises an elastic, tubular, conical clamping mechanism attached to said shield formed for attachment to and detachment from a light wand.

6. The device of claim 5 wherein said clamping mechanism is positioned eccentrically on one surface of said shield.

7. The device of claim 5 wherein said clamping mechanism departs from a plane of the shield at an irregular angle of the order of 15°.

8. The device of claim 5 wherein said tubular clamping mechanism is adapted to receive and engage light wands of various diameters inserted through said clamping mechanism.

9. The device of claim 5 wherein said tubular clamping mechanism is padded by an elastic collet to fit and clamp light wands of a diameter smaller than said aperture.

10. The device of claim 5 which further comprises an annular ring of elastic material stretched around a distal end of said clamping mechanism.

11. The device of claim 5, which further comprises an elastic annular ring at a distal end of said clamping mechanism said clamping mechanism having a lumen formed with a groove capable of holding a replaceable lens.

12. A light shield comprising an aperture adapted for receiving and engaging a light wand and a reflecting zone corrugated in the manner of a Fresnel lens to collect and redirect stray light reflected from a work area to a focused and functional position.

13. The light shield of claim 12 wherein said reflecting zone of the shield is heavily coated with reflective material to reflect or block all reflected light.

14. The light shield of claim 12 wherein said reflective material on the reflective zone of the shield is applied to a proximal first surface of said shield.

15. The light shield of claim 12 wherein said reflective material on the reflective zone is applied to a distal second surface of said shield.

16. A device for protecting the eyes of operators and bystanders from such harm as may result from viewing bright light emanating from a light wand to a work area and reflected back from that work area, comprising:

a light shield, said shield having two opposing major surfaces and being adapted to engage a light wand, and a reflecting zone corrugated in the manner of a Fresnel lens to collect and redirect stray light reflected from a work area to a focused and functional position.

17. The light shield of claim 16 wherein said reflecting zone of the shield is heavily coated with reflective material to reflect or block all reflected light.

18. The light shield of claim 16 wherein said reflective material on the reflective zone of the shield is applied to a proximal first surface of said shield.

19. The light shield of claim 16 wherein said reflective material on the reflective zone is applied to a distal second surface of said shield.

* * * * *